US011620212B2

(12) United States Patent
Schwenker et al.

(10) Patent No.: US 11,620,212 B2
(45) Date of Patent: Apr. 4, 2023

(54) METHOD FOR VALIDATING A MEDICAL APPLICATION, END USER DEVICE AND MEDICAL SYSTEM

(71) Applicant: Roche Diabetes Care, Inc., Indianapolis, IN (US)

(72) Inventors: Kai-Oliver Schwenker, Mannheim (DE); Thomas Eissenloeffel, Mannheim (DE); Bimal Thayyil, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 334 days.

(21) Appl. No.: 16/824,463

(22) Filed: Mar. 19, 2020

(65) Prior Publication Data

US 2020/0218641 A1 Jul. 9, 2020

Related U.S. Application Data

(63) Continuation of application No. PCT/EP2018/075386, filed on Sep. 19, 2018.

(30) Foreign Application Priority Data

Sep. 20, 2017 (EP) .................................... 17192247

(51) Int. Cl.
*G06F 8/61* (2018.01)
*G06F 11/36* (2006.01)
(Continued)

(52) U.S. Cl.
CPC ............ *G06F 11/3688* (2013.01); *G06F 8/61* (2013.01); *G16H 40/40* (2018.01); *G16H 40/67* (2018.01); *H04L 9/3247* (2013.01)

(58) Field of Classification Search
None
See application file for complete search history.

(56) References Cited

U.S. PATENT DOCUMENTS 6,775,536 B1   8/2004   Geiger et al.
9,185,554 B2   11/2015  Nagpal et al.
(Continued)

OTHER PUBLICATIONS

International Search Report and Written Opinion of the International Searching Authority, PCT/EP2018/075386, dated Oct. 29, 2018, 11 pages.

*Primary Examiner* — Marina Lee
(74) *Attorney, Agent, or Firm* — Bose McKinney & Evans LLP (57) ABSTRACT

An inventive method for validating an end user device for use with a medical application. A medical application and a validation application are received in the end user device and the validation application is then executed, which includes: (i) determining the hardware and software environment of the end user device; (ii) providing a validation process compatible with the hardware and software environment; (iii) executing a test mode of the medical application; (iv) running the validation process during the test mode; and (v) determining from running the validation process whether the medical application is compatible with the end user device. When the medical application is determined to be compatible with the end user device, a validation report is generated and stored in the end user device and/or a server. When the medical application is determined to be incompatible with the end user device, the medical application is at least partially blocked.

11 Claims, 5 Drawing Sheets

(51) Int. Cl.
*G16H 40/67* (2018.01)
*G16H 40/40* (2018.01)
*H04L 9/32* (2006.01)

(56) References Cited

U.S. PATENT DOCUMENTS

| | | | |
|---|---|---|---|
| 11,456,076 B2* | 9/2022 | Holmquist | G16H 40/67 |
| 2010/0318379 A1* | 12/2010 | Demopulos | G16H 15/00 |
| | | | 705/3 |
| 2014/0059677 A1* | 2/2014 | Urness | G16Z 99/00 |
| | | | 718/1 |
| 2016/0188318 A1 | 6/2016 | Li et al. | |
| 2016/0203067 A1* | 7/2016 | Marko | G06F 11/2268 |
| | | | 714/37 |
| 2017/0132120 A1* | 5/2017 | Salameh | G06F 11/3616 |
| 2017/0147313 A1 | 5/2017 | Casciano et al. | |
| 2017/0319861 A1* | 11/2017 | Golden | A61B 5/7465 |

\* cited by examiner

FIG. 5

METHOD FOR VALIDATING A MEDICAL APPLICATION, END USER DEVICE AND MEDICAL SYSTEM

RELATED APPLICATIONS

This application is a continuation of PCT/EP2018/075386, filed Sep. 19, 2018, which claims priority to EP 17 192 247.9, filed Sep. 20, 2017, both of which are incorporated herein by reference in their entirety.

BACKGROUND

The present disclosure refers to a method for validating a medical application on an end user device configured for data communication with a medical device by the medical application, an end user device and a medical system.

Users of a medical device may employ end user devices on which a medical application is running for communicating with medical device. The medical application can be used to manage data communication between the medical device of the end user device, such as transmitting measurement data acquired by the medical device to the end user device or sending commands generated from user input from the end user device to the medical device. For example, a smartphone of a diabetes patient may be configured to run a medical application that collects glucose values from a glucose meter and is also used to configure the glucose meter. As data communication with medical devices is concerned, safety and security of medical application is an important issue.

U.S. Publication No. 2017/0147313 A1 discloses systems and methods for application software system installation in a user device, wherein the desired App includes App configuration data to be entered by the intended user through a user interface. An App configuration data validation processor verifies that the user has correctly entered the desired App configuration data. When the user requests an install of the desired App to a particular device, the system digitally signs the App with the validated embedded data in an App configuration file, which digital signature must be validated by the intended device before installation of the App is accepted on the device. After both validation of the configuration data and the digital signature, the user is then permitted to execute the App on the intended device.

In U.S. Pat. No. 9,185,554 B2, systems and methods for managing applications on an appliance are disclosed. A server is in communication with appliances. The server is also coupled to databases which include appliance information, as well as application data. A user may authenticate using the appliance. A set of permissions may be associated with the user. The server then supervises information exchanged between the appliance and the server, as well as application functionality upon the appliance, by supplementing the applications downloaded to the appliance with supplemental code, referred to as an AppGuard. The AppGuard is tailored, using information related to the appliance, to the appliance type in order to ensure proper functionality. The AppGuard is executed upon installation, and collects device information for validation. After validation, the application may be run. Additionally, management of the applications may include augmenting, deleting, disabling or authorizing the application.

U.S. Pat. No. 6,775,536 B1 describes a method in which a wireless domain sets a security policy for all mobile communication devices within the domain by use of a system entry proxy server. A developer makes an application or code segment available at a developer station. The application is certified by a certificate defining a developer security setting. The user of the mobile communication device initiates a download of the application so that it can be installed onto the mobile communication device. The application is downloaded through the system entry proxy server which authenticates the application, then re-certifies it with a compact certificate including an operator defined security policy. In this way the operator can control which resources of the mobile communication device are accessed by all applications coming into the wireless domain.

U.S. Publication No. 2017/0132120 A1 discloses systems, methods, and articles for determining compatibility of a mobile application and operating system on a mobile device. In some aspects, a method includes receiving one or more data values from a mobile device having a mobile medical software application installed thereon, the data value(s) characterizing a version of the software application, a version of an operating system installed on the mobile device, and one or more attributes of the mobile device; determining whether the mobile medical software application is compatible with the operating system by at least comparing the received data value(s) to one or more test values in a configuration file; and sending a message to the mobile device based on the determining, the message causing the software application to operate in one or more of a normal mode, a safe mode, and a non-operational mode.

In U.S. Publication No. 2016/0188318 A1, a method for upgrading medical equipment is described. The method may include: according to a first target upgrading identification in a software upgrading package, determining a first target equipment number corresponding to the first target upgrading identification. The table of upgrading identifications can include association between upgrading identifications and equipment numbers of the medical equipment. The method further includes sending the software upgrading package to a first target medical equipment corresponding to the first target equipment number to allow the first target medical equipment to upgrade itself according to the software upgrading package.

SUMMARY

The present disclosure teaches a method for validating a medical application on an end user device configured for data communication with a medical device by a medical application that provides enhanced safety and functionality. Further, an end user device for data communication with a medical device by a medical application and a medical system is disclosed.

According to an aspect, a method for validating a medical application on an end user device configured for data communication with a medical device by the medical application is provided. The method comprises: receiving a medical application in an end user device, the medical application being a software-implemented application and configured to provide for data communication between the end user device and a medical device; receiving a validation application in the end user device, the validation application being a software-implemented application; and at least in case of a first execution of the medical application in the end user device, executing the validation application. Executing the validation application comprises: determining a software environment provided to the user device; determining a hardware environment provided to the user device; in response to the software and hardware environment determined, setting up a validation process for testing the software and hardware environment to be compatible with execution requirements for executing the medical application in the end user device; and testing the software and hardware environment according to the validation process. The method for validating a medical application further comprises executing the medical application in the end user device, if the software and hardware environment are tested compatible with the execution requirements by the validation application, and blocking the medical application from execution in the end user device, if the software and hardware environment are tested not compatible with the execution requirements by the validation application. The executing of the medical application comprises generating a validation report in the end user device, the validation report indicating the medical application to be validated, transmitting the validation report to a server device, and storing the validation report in a non-editable data format in at least one of the end user device and the server.

According to another aspect, an end user device for data communication with a medical device by a medical application is provided. The end user device is having one or more processors; a medical application, the medical application being a software-implemented application and configured to provide for data communication between the end user device and a medical device; and a validation application. The validation application is a software-implemented application and is configured, at least in case of a first execution of the medical application in the end user device, to: determine a software environment provided to the user device; determine a hardware environment provided to the user device; in response to the software and hardware environment determined, set up a validation process for testing the software and hardware environment to be compatible with execution requirements for executing the medical application in the end user device; and test the software and hardware environment according to the validation process. The medical application is further configured to be executed by the one or more processors, if the software and hardware environment are tested compatible with the execution requirements by the validation application, and to be blocked from execution by the one or more processors, if the software and hardware environment are tested not compatible with the execution requirements by the validation application. The end user device is further configured to generate a validation report when the medical application is executed, the validation report indicating the medical application to be validated, and transmit the validation report to a server device, the validation report being stored in a non-editable data format in at least one of the end user device and the server.

According to a further aspect, a medical system is provided. The medical system comprises a medical device and the end user device.

According to the technologies proposed, a hardware and software environment provided to an end user device are tested to be compatible with execution requirements for executing a medical application using a validation application. The validation application allows executing the medical application or blocks the medical application from execution in response to the testing. The validation application may be understood or referred to as enveloping the medical application and screening it from the outside, i.e., interaction with software and hardware components external to the medical application itself. The validation application may therefore also be referred to as an Envelope App. If the software and hardware environment are tested compatible with the execution requirements by the Envelope App, the envelope is opened, i.e., execution the medical application is allowed.

The receiving of the medical application may be performed prior to or after the receiving the validation application. Alternatively, the receiving the medical application and the receiving the validation application may be performed, at least partly, at the same time. The receiving the medical application may be performed prior to or after the executing the validation application. Alternatively, the receiving the medical application may be performed while executing the validation application. For example, part of the testing the software and hardware environment, which may also respectively be referred to as a software and a hardware configuration, may be performed before the receiving the medical application and another part of the testing the software and hardware environment may be performed after the receiving the medical application.

The end user device may be a smart phone, personal computer, tablet computer, diabetes management device or any other end user device that may be communicatively coupled to a medical device to transmit data to or receive data from the medical device.

The medical application and the validation application are received in the end user device. The executing of the validation application may therefore be referred to as an infield validation. As the validation application is executed at least in case of a first execution of the medical application, the executing the validation application may be referred to as an on demand validation.

The validation report may comprise information on the hardware and/or software environment provided to the user device and/or information on test results determined testing the software and/or hardware environment.

For storing the validation report in a non-editable data format in at least one of the end user device and the server, the validation report may, for example, include a security signature and may only be accessed using a secure code. The validation report may be encrypted using a security signature and a secure code may be needed to decrypt the validation report. The validation report may serve as proof that a validation process has taken place, for example in front of official bodies. For example, the validation report may be encrypted by the validation application using a public key supplied by an official body, such as a government agency concerned with the safety of medical devices, and then transmitted to the official body. The official body may then decrypt the validation report using a private key that is not known outside the official body and analyze the validation report to ensure that official requirements regarding validation were fulfilled.

The blocking of the medical application from execution may comprise generating a non-validation notification in the end user device, the non-validation notification indicating the medical application not to be validated, and outputting the non-validation notification through an output device of the end user device. The non-validation notification may comprise audio and/or video data. For example, the non-validation notification may comprise an alarm tone played through a speaker of the user device and a text message indicating non-validation displayed on a display of the user device.

Alternatively or in addition, the blocking of the medical application from execution may comprise generating a validation report in the end user device, the validation report indicating the medical application to not be validated, and transmitting the validation report to a server device. The validation report may comprise information on the hardware and/or software environment provided to the user device and/or information on test results determined testing the software and/or hardware environment. The validation report may be stored in a non-editable data format in at least one of the end user device and the server. Features described above with regard to the validation report indicating the medical application to be validated may apply to the validation report indicating the medical application to not be validated, accordingly.

The setting up of the validation process may comprise selecting the validation process from a plurality of predefined validation processes, each of the predefined validation processes assigned to at least one software environment and/or at least one hardware environment. Predefined validation processes from which the validation process may be selected may be provided in the end user device and/or a server. The predefined validation processes may be different from each other with regard to the software environment and/or the hardware environment that they are assigned to. For example, different predefined validation processes may be assigned to a certain model of end user device, a certain version of an operating system and a certain version of an operating system running on a certain model of end user device, respectively, each of the predefined validation processes being adapted to the respective model of end user device, version of an operating system or combination thereof.

As an alternative or in addition to selecting the validation process from a plurality of predefined validation processes, the setting up of the validation process may comprise assembling the validation process from one or more predefined validation process modules. Each of the predefined validation process modules may be assigned to at least one software environment and/or at least one hardware environment. For example, different predefined validation process modules may each be assigned to a certain type of user interface (such as a touchscreen, a speaker or a display) provided to a user device. If it is determined that the hardware environment provided to the user device includes such a type of user interface, the corresponding predefined validation process module may be included in the assembly of the validation process or may be added to a predefined validation process.

A preselection of predefined validation processes and/or predefined validation process modules may be made at the time of receiving the validation application and/or the medical application. The preselection of predefined validation processes and/or predefined validation process modules may be received from a server together with the validation application and/or the medical application and stored in the end use device. In such an embodiment, the validation process may be selected and/or assembled from the preselection of predefined validation processes and/or predefined validation process modules stored on the end user device. For example the preselection may be made based on information transmitted by the end user device when receiving the validation application and/or the medical application.

The blocking of the medical application from execution may comprise executing the medical application with reduced functionality in the end user device. Executing the medical application with reduced functionality may comprise blocking at least one functionality provided by the medical application from execution in the end user device, and executing at least one other functionality provided by the medical application in the end user device. A determination whether a functionality shall be executed or shall be blocked may be made based on the software environment and/or the hardware environment determined by the validation application. Functionalities that may be executed and/or blocked may include functionalities related to data communication between the end user device and the medical device, such as receiving measurement data from the medical device in the end user device and submitting control data from the end user device to the medical device.

In an exemplary embodiment, executing the medical application with reduced functionality in the end user device comprises allowing the end user device to receive measurement data from the medical device and blocking the end user device from transmitting control data to the medical device. In a different embodiment, all data communication between the end user device and the medical device may be blocked. In such an embodiment, only functionality regarding an interaction between the user and the end user device may be allowed. Dummy data may be provided to simulate data transmission functionality.

The method may comprise re-executing the validation application. The re-executing the validation application may comprise determining at least one of a present software environment and a present hardware environment provided to the user device and, if one of the present software environment and the present hardware environment is determined to be different from the software environment and the hardware environment, respectively, setting up a present validation process for testing the present software and/or the present hardware environment to be compatible with execution requirements for executing the medical application in the end user device, and testing the present software and/or the present hardware environment according to the validation process.

Following, the medical application may be executed in the end user device, if the software and hardware environment are tested compatible with the execution requirements by the validation application, and the medical application may be blocked from execution in the end user device, if the software and hardware environment are tested not compatible with the execution requirements by the validation application The re-executing of the validation application may comprise terminating re-execution of the validation application, if none of the present software environment and the present hardware environment is determined to be different from the software environment and the hardware environment, respectively.

The re-executing of the validation application may comprise, if one of the present software environment and the present hardware environment is determined to be different from the software environment and the hardware environment, blocking the medical application from execution and terminating re-execution of the validation application. An output signal may be generated informing the user of the blocking of the medical application from execution. In such an embodiment, the medical application may be blocked from execution until a full re-execution of the validation app is triggered comprising setting up a present validation process for testing the present software and/or the present hardware environment to be compatible with execution requirements for executing the medical application in the end user device and testing the present software and/or the present hardware environment according to the validation process, resulting in blocking or allowing execution of the medical application. For example, full re-execution of the validation app may be triggered in response to a user input.

Determining a present software environment and/or a present hardware environment may become necessary in certain embodiments because changes in the software environment and/or the hardware environment may influence compatibility with execution requirements for executing the medical application.

The validation application may be re-executed in set intervals. For example, such intervals may be time intervals, such as a time passed since the validation application has last been executed, or a different type of interval, such as a number of times the medical application has been executed since the validation has last been executed. The validation application may be re-executed every time the medical application is executed.

Alternatively or additionally, the validation application may be re-executed in response to an event. One example of such an event is a user input prompting the re-execution of the validation application. Another example of an event is receiving, in the end user device, data prompting re-execution of the validation application. Such data may be received, for example, from a server or the medical device. Data prompting re-execution of the validation application may also be received from another validation application associated with another medical application running on the same user device upon execution of the other validation application. Yet another example of an event that may trigger re-execution of the validation application is a probable change in the hardware environment and/or the software environment. For example, a change in data received from a user input device by the medical application may indicate that there may have been a change in hardware with regard to the input device. In response to the determination of such change in data received by the medical application, re-execution of the validation application may be triggered.

The method may comprise providing a white listing of at least one of software components and hardware components allowed for being provided in the software environment and the hardware environment, respectively, provided to the end user device, and determining whether at least one of a hardware component and a software component determined to be provided in the software environment and the hardware environment, respectively, is in the white listing.

If it is determined that a hardware component, a software component, or a combination of hardware components and/or software components is in the white listing, testing the software environment and/or the hardware environment may be foregone insofar as the component or combination of components determined to be in the white listing is regarded. Alternatively or additionally, if it is determined that a certain hardware component, a certain software component, or a certain combination of hardware components and/or software components is in the white listing, testing the software environment and/or the hardware environment may be foregone entirely and the medical application may be executed.

The white listing may be provided prior to executing the validation application. Alternatively, the white listing may be provided during the execution of the validation application. The white listing may be dynamically updated. For example, the white listing may be updated via a server. The white listing may be updated by adding new components when the components are determined to be compatible with execution requirements for executing the medical application and/or by deleting components when the components are determined to no longer be compatible with execution requirements for executing the medical application. New components that may be added to the white listing may comprise components that are newly introduced or components that have changed, for example software components that have been updated. Components may be deleted when they are determined to no longer be compatible with execution requirements for executing the medical application after the component has changed, for example when a software component has been updated. Alternatively or additionally, components may be added to or deleted from the white listing when it is determined that they are compatible or that they are no longer compatible with execution requirements for executing the medical application after the medical application has changed, for example after the medical application has been updated.

Dynamically updating the white listing may include adding or deleting a component to the white listing in response to a validation application, executed in an end user device, determining the component to be compatible or not compatible, respectively, with execution requirements for executing a medical application and providing the updated white listing for use in other validation applications, executed on other end user devices, for example via a server.

The method may comprise providing a black listing of at least one of software components and hardware components not allowed for being provided in the software environment and the hardware environment, respectively, provided to the end user device, and determining whether at least one of a hardware component and a software component determined to be provided in the software environment and the hardware environment, respectively, is in the black listing.

If it is determined that a hardware component, a software component, or a combination of hardware components and/or software components is in the black listing, testing the software environment and/or the hardware environment may be foregone and the medical application may be blocked from execution in the end user device. Alternatively, if it is determined that a hardware component, a software component, or a combination of hardware components and/or software components is in the black listing, testing the software environment and/or the hardware environment may be performed but, if the software and hardware environment are otherwise tested compatible with the execution requirements by the validation application, only limited execution of the medical application in the end user device may be allowed. For example, functionality with regard to the hardware component, the software component, or the combination of hardware components and/or software components determined to be in the black listing may be excluded from execution.

The black listing may be provided prior to executing the validation application. Alternatively, the black listing may be provided during the execution of the validation application. The black listing may be dynamically updated. For example, the black listing may be updated via a server. The black listing may be updated by adding new components when the components are determined to not be compatible with execution requirements for executing the medical application and/or by deleting components when the components are determined to no longer be incompatible with execution requirements for executing the medical application. New components that may be added to the black listing may comprise components that are newly introduced or components that have changed, for example software components that have been updated. Components may be deleted when they are determined to now be compatible with execution requirements for executing the medical application after the component has changed, for example when a software component has been updated. Alternatively or additionally, components may be added to or deleted from the black listing when it is determined that they are no longer compatible or that they are now compatible with execution requirements for executing the medical application after the medical application has changed, for example after the medical application has been updated.

Dynamically updating the black listing may include adding or deleting a component to the black listing in response to a validation application, executed in an end user device, determining the component to be not compatible or compatible, respectively, with execution requirements for executing a medical application and providing the updated black listing for use in other validation applications, executed on other end user devices, for example via a server.

In an embodiment, the providing a black listing and/or the providing a white listing and the determining whether at least one of a hardware component and a software component determined to be provided in the software environment and the hardware environment, respectively, is in the black listing and/or the white listing may be performed prior to and separate from the executing the validation application. Based on the determining whether at least one of a hardware component and a software component is in the black listing and/or the white listing, a feedback may be provided to the user prior to the actual validation process. In such an embodiment the white listing and/or the black listing may or may not be used in the validation process as described above.

The executing of the validation application may comprise executing a user interaction routine configured to test a user interface provided in the end user device. In an exemplary embodiment, a request for a user input may be outputted to the user via a user interface. A user input may then be received and it may be determined whether the user input was correctly received. For example, a user may be prompted, via a message displayed on a touchscreen of the end user device, to make a certain input, such as a pattern drawn by the user with his finger, via the touchscreen. The input may then be compared to a reference and it may be determined whether the input was correctly received based on a deviation of the input from the reference. Thus, correct calibration of the touchscreen may be determined. In another example of a user interaction routine, the user may be prompted, via a speaker of the end user device, to make a certain input, such as repeating a sentence, to a microphone of the end user device. Based on comparing the input received to a reference, correct functioning of the microphone and the speaker may be determined. Other examples of user interaction routines may be implemented using any user interface or combination of user interfaces provided in the end user device.

The executing of the validation application may comprise executing the medical application in demonstration mode. Demonstration mode may comprise limiting functionality of the medical application. Executing the medical application in demonstration mode may comprise blocking at least one functionality provided by the medical application from execution and executing at least one other functionality provided by the medical application. Functionalities that may be executed and/or blocked may include functionalities related to data communication between the end user device and the medical device, such as receiving measurement data from the medical device in the end user device and submitting control data from the end user device to the medical device. For example, demonstration mode may comprise allowing the end user device to receive measurement data from the medical device and blocking the end user device from transmitting control data to the medical device. Alternatively, all data communication between the end user device and the medical device may be blocked. In demonstration mode, only functionality regarding an interaction between the user and the end user device may be allowed. Dummy data may be provided to simulate data transmission functionality. The medical application may be executed in demonstration mode to test a user interface under realistic conditions. Alternatively or additionally, the medical application may be executed in demonstration mode for testing the software and hardware environment according to the validation process under realistic conditions. For example, the processing speed of a hardware component, such as a processor, may be determined under realistic conditions in demonstration mode.

According to the technologies proposed, a hardware and software environment provided to an end user device are tested to be compatible with execution requirements for executing a medical application. Compatibility with execution requirements may refer to any, all, or a combination of several parameters. For example, it may be tested that none of the software and/or hardware components that form part of the hardware and/or software environment are excluded from use with the medical application. Components may be excluded because they are on a list of excluded components and/or because they fail certain tests. Such tests may include determining the speed of execution of software components, processing power of hardware components such as processors or graphics adapters, data throughput of transceiver devices or bus systems and/or security parameters of hardware and/or software. Security parameters that may be tested may encompass, for example, level of hardware or software based data encryption for data storage and/or transmission and/or access to hardware, software and/or stored data by a third party application installed on the user device. It may be determined that the software environment includes third-party apps that are known to be vulnerable to hacking or that are known to disclose sensitive data to third parties and therefore, the software environment may not be compatible with execution requirements.

Testing of compatibility with execution requirements may, alternatively or additionally, be based on whether the combination of software and/or hardware components that was determined is allowed. For example, a certain processor may be allowed, but a combination of this processor with a certain software module, that is known to demand a substantive amount of the processor's processing power, may not be allowed. In further examples, the combination of a certain third-party application with a certain operating system or the combination of a certain processor with a certain graphics adapter may not be allowed.

Determining the hardware and software environment may comprise determining one or any combination of a make and model of the end user device, a processor architecture, storage devices provided in the end user device, storage devices provided outside and associated with the end user device, communication interfaces (such as Bluetooth and/or USB), user interfaces (such as buttons, display, touchscreen and/or speaker, including parameters associated therewith, such as dimension and pixel density of a display), type and version of the operating system, additional software libraries provided in the end user device and other parameters suitable to test the software and hardware environment to be compatible with execution requirements for executing the medical application.

In an exemplary embodiment, the end user device may be configured for data communication by the medical application with a medical device that is configured to provide continuous monitoring data indicative of an analyte in a bodily fluid of the user. Data communication may comprise transmitting monitoring or measurement data and/or transmitting control data, such as data for configuring the medical device (for example defining a measurement interval for acquiring continuous monitoring data).

Continuous monitoring data may be provided by a sensor that is a fully or partially implanted sensor for continuous glucose monitoring (CGM). In general, in the context of CGM, an analyte value or level indicative of a glucose value or level in the blood may be determined. The analyte value may be measured in an interstitial fluid. The measurement may be performed subcutaneously or in vivo. CGM may be implemented as a nearly real-time or quasi-continuous monitoring procedure frequently or automatically providing/updating analyte values without user interaction. In an alternative embodiment, analyte may be measured with a biosensor in a contact lens through the eye fluid or with a biosensor on the skin via transdermal measurement in sudor. A CGM sensor may stay in place for several days to weeks and then must be replaced.

The medical application may display information to the end user via a display device of the end user device. The displaying information may comprise displaying the information via a graphical user interface of the medical application. The graphical user interface of the medical application may comprise elements that are independent of the software environment and/or the hardware environment. For example, the medical application may display information via a graphical user interface with a size and/or aspect ratio that does not change across hardware and/or software environments, such as different operating systems or changing display settings. Alternatively or additionally, the medical application may be configured to display any or all other elements or combination of elements of a graphical user interface of the medical application, such as type font, font size, color scheme and the like, independently of the software environment and/or the hardware environment. The medical application may be configured to override display settings of the software environment and/or the hardware environment. For example, the medical application may be configured to override settings of a display theme set in the end user device, for example a mobile phone of the end user.

Setting up the validation process may comprise setting up a reduced validation process in which the software and hardware environment are not tested to be compatible with one or more execution requirements for executing the medical application device. The one or more execution requirements for which compatibility is not tested may comprise one or more execution requirements for which testing is not necessary because information is displayed on the end user device via a graphical user interface comprising elements that are independent of the software environment and/or the hardware environment.

With regard to the end user device and the system, the alternative embodiments described above may apply mutatis mutandis.

A method for validating a medical application on an end user device configured for data communication with a medical device by the medical application may be provided. The method comprises: receiving a medical application in an end user device, the medical application being a software-implemented application and configured to provide for data communication between the end user device and a medical device; receiving a validation application in the end user device, the validation application being a software-implemented application; and at least in case of a first execution of the medical application in the end user device, executing the validation application. Executing the validation application comprises: determining a software environment provided to the user device; determining a hardware environment provided to the user device; in response to the software and hardware environment determined, setting up a validation process for testing the software and hardware environment to be compatible with execution requirements for executing the medical application in the end user device; and testing the software and hardware environment according to the validation process. The method for validating a medical application further comprises executing the medical application in the end user device, if the software and hardware environment are tested compatible with the execution requirements by the validation application, and blocking the medical application from execution in the end user device, if the software and hardware environment are tested not compatible with the execution requirements by the validation application.

With regard to such method, the additional aspects described above with regard to a method for validating a medical application on an end user device configured for data communication with a medical device by the medical application may apply, mutatis mutandis.

An end user device for data communication with a medical device by a medical application may be provided. The end user device is having one or more processors; a medical application, the medical application being a software-implemented application and configured to provide for data communication between the end user device and a medical device; and a validation application. The validation application is a software-implemented application and is configured, at least in case of a first execution of the medical application in the end user device, to: determine a software environment provided to the user device; determine a hardware environment provided to the user device; in response to the software and hardware environment determined, set up a validation process for testing the software and hardware environment to be compatible with execution requirements for executing the medical application in the end user device; and test the software and hardware environment according to the validation process. The medical application is further configured to be executed by the one or more processors, if the software and hardware environment are tested compatible with the execution requirements by the validation application, and to be blocked from execution by the one or more processors, if the software and hardware environment are tested not compatible with the execution requirements by the validation application.

With regard to such end user device, the additional aspects described above may apply, mutatis mutandis.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
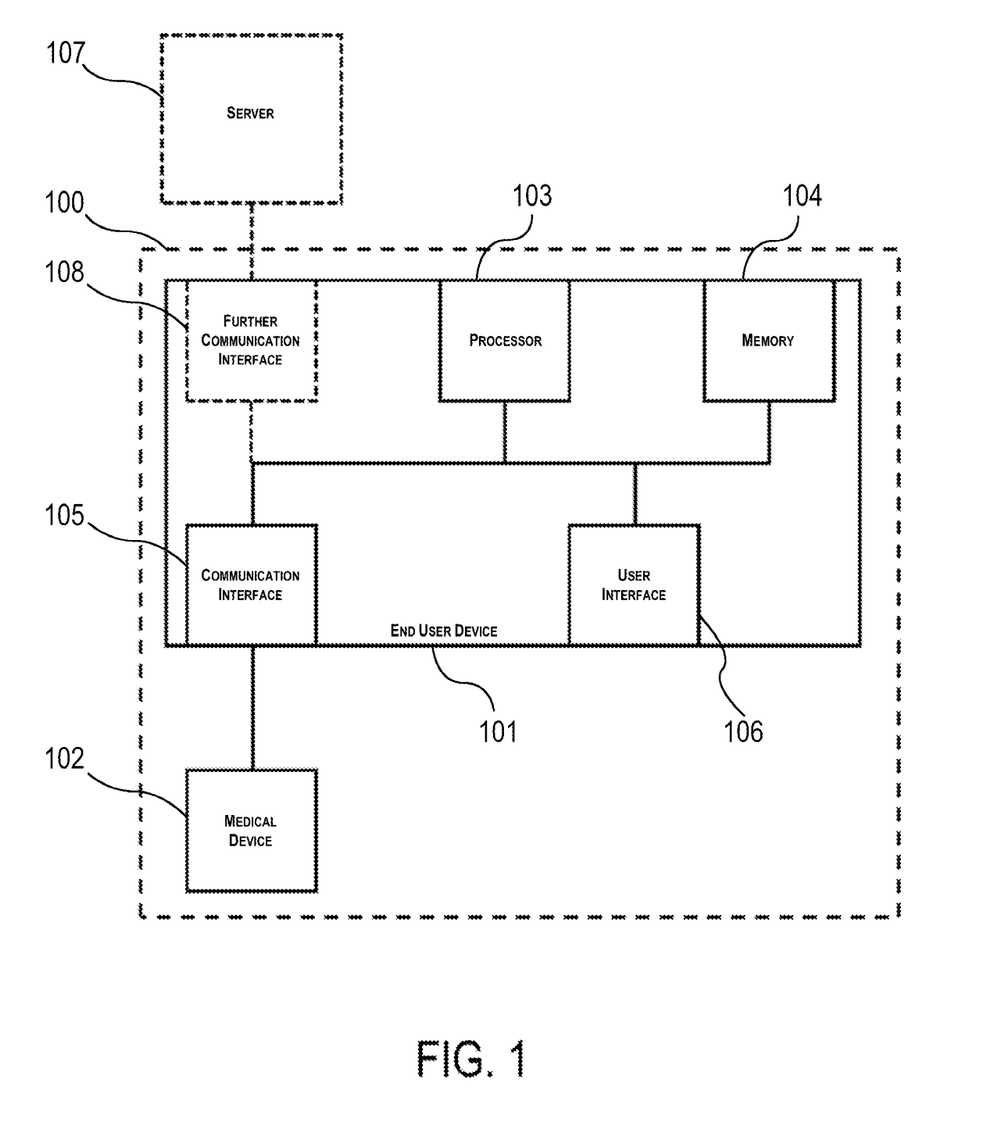
FIG. 1 a schematic representation of a medical system.

FIG. 1 shows a schematic representation of a medical system 100 comprising an end user device 101 and a medical device 102. In the embodiment shown, the medical device 102 is a blood glucose meter for continuous glucose monitoring. In alternative embodiments, the medical device 102 may be an insulin pump or any other medical device that may be used with an end user device 101 to receive data from the medical device 102 in the end user device 101 or send data from the end user device 101 to the medical device 102.

The end user device 101 may be a smart phone, personal computer, tablet computer, diabetes management device or any other end user device that may be communicatively coupled to a medical device 102 to transmit data to or receive data from the medical device 102. The end user device 101 comprises a processor 103 and a memory 104. In alternative embodiments, more than one processor 103 and/or more than one memory 104 may be provided. A medical application as well as a validation application may be stored in the memory 104 and may be retrieved from the memory 104 and executed by the processor 103.

The end user device 101 further comprises a medical device communication interface 105 to receive data from and transmit data to the medical device 102. Medical device communication interface 105 may be configured to provide a connection to medical device 102 via a wire. Alternatively or additionally, medical device communication interface 105 may be configured to provide a wireless connection with medical device 102.

Additionally, a user interface 106 is provided in end user device 101. The user interface 106 may comprise a single interface device or a plurality of interface devices. The plurality of interface devices may comprise input devices, output devices and combined input/output devices. For example, the user interface 106 may comprise a touchscreen, a display, a keyboard, a computer mouse, a display, a speaker, a microphone, and/or any other device via which an input may be received from a user or an output may be provided to a user.

The end user device 101 may further be coupled, wirelessly or via a wire, to a server 107 or other external device by a further communication interface 108.

Figure 2:
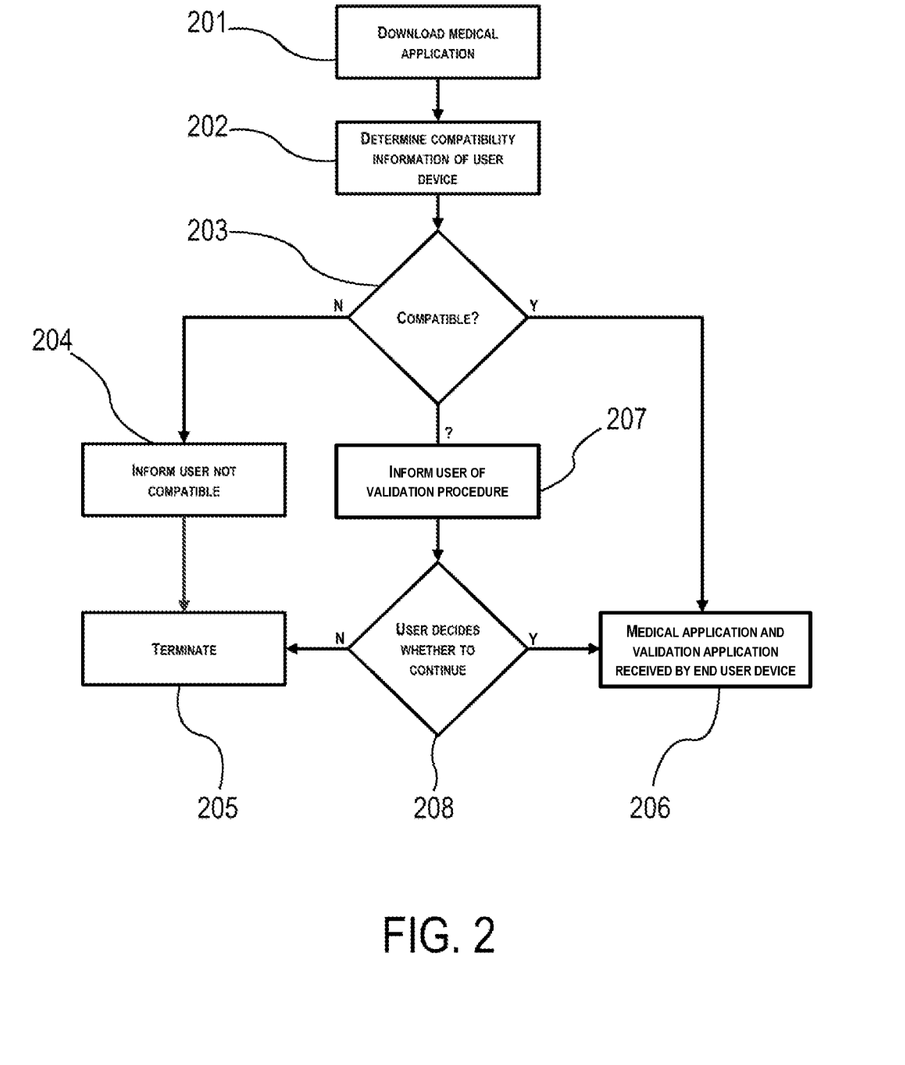
FIG. 2 a flow diagram for steps of a method for validating a medical application.

FIG. 2 is a flow diagram that illustrates steps of a method for validating a medical application on an end user device 101 configured for data communication with a medical device 102 by the medical application. Stated another way, the method shown in FIG. 2 validates the end user device for use with the medical application.

In step 201, a user prompts the end user device 101 to download the medical application. In step 202, in response to the user prompt, prior information on the compatibility of the end user device 101 for the medical application is determined by determining device parameters, such as device model number, location and/or platform version, and receiving a white listing and a black listing from a server 107. The black listing and the white listing contain values for the parameters and/or combinations of values of the parameters indicating whether the end user device 101 is compatible, in the case of the white listing, or not compatible, in the case of the black listing, for the medical application. Following, in step 203, it is determined by the end user device 101, whether each device parameter is compatible, based on the white listing, not compatible, based on the black listing, or whether compatibility cannot be determined based on the black listing and the white listing. Alternatively or additionally, device parameters may be transmitted to the server 107 and determination regarding compatibility based on the white listing and the black listing may be performed in the server 107.

If it is determined, based on the black listing, that the end user device 101 is not compatible for the medical application, the user is informed in step 204 by an output via a user interface 106 of the end user device 101 that the device is not supported for the medical application and the method terminates in step 205. If it is determined, based on the white listing, that the end user device 101 is compatible for the medical application, the medical application and a validation application are received by the end user device 101 in step 206. If compatibility cannot be determined based on the black listing and the white listing, the user is informed in step 207, by an output via the user interface 106 of the end user device 101, of a validation procedure and pre-requisites for the validation procedures using the validation app. Based on the information provided to the user, the user decides in step 208 whether he would like to continue with the procedure and provides a corresponding input to the end user device 101 via user interface 106. If the user decides not to continue with the procedure, the method terminates in step 205. If the user decides to continue with the procedure, the medical application and the validation application are received by the end user device 101 in step 206.

Figure 3:
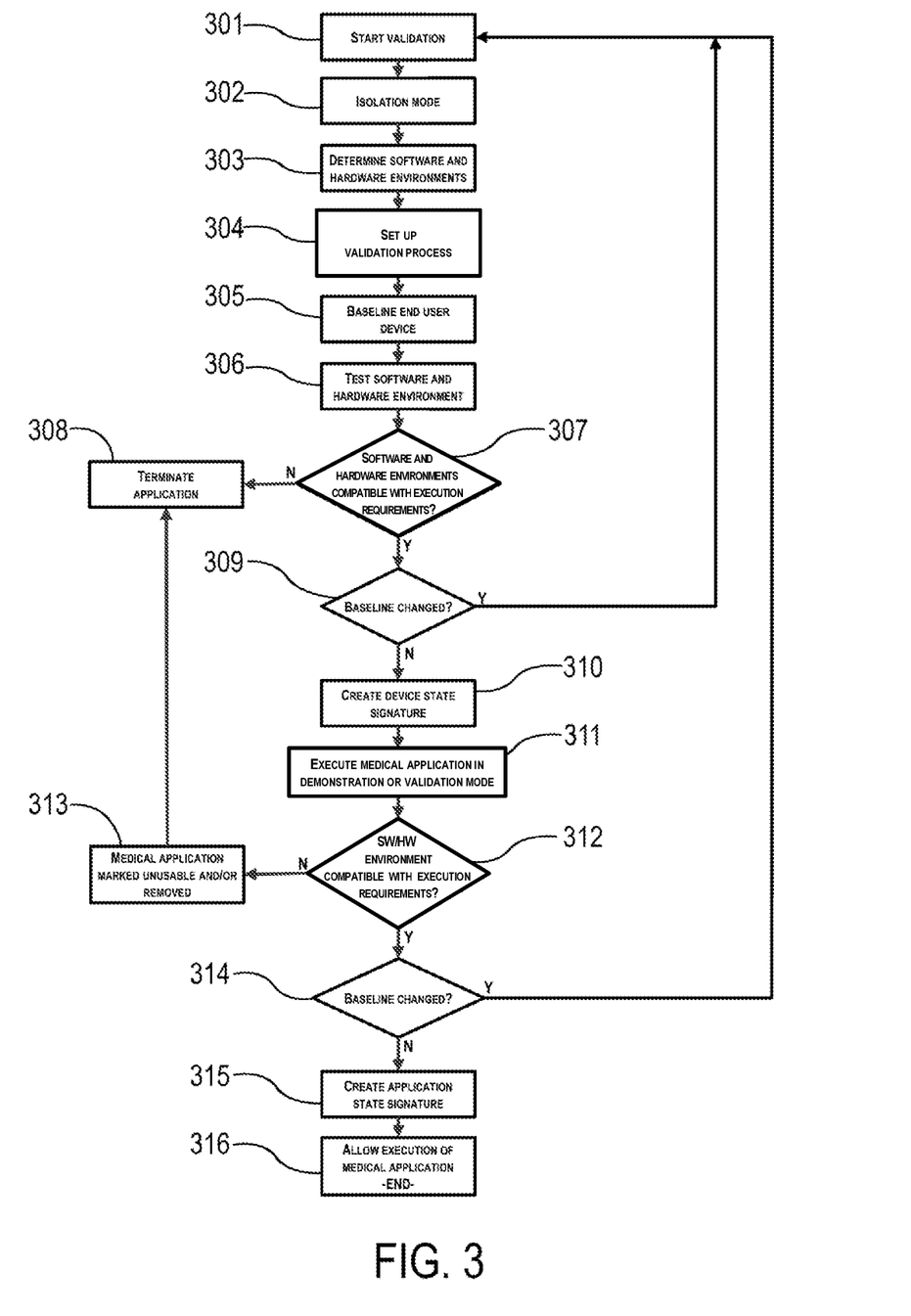
FIG. 3 a flow diagram for steps of another method for validating a medical application.

FIG. 3 is a flow diagram illustrating steps of another method for validating a medical application on an end user device 101 configured for data communication with a medical device 102 by the medical application.

In step 301, the validation application is executed and the validation is started. Additionally, the user may be prompted to confirm starting the validation. If the user confirms, the validation may then be started. If the user does not confirm starting the validation, the execution of the validation application may be terminated.

The end user device is taken to an isolation mode in step 302. In the isolation mode, any external influence on the user device, such as data transmissions to or from the device 101 via third-party applications, is blocked. Alternatively, step 302 may be omitted and the end user device 101 may not be taken to isolation mode.

Following, in step 303, the software environment and the hardware environment provided to the end user device 101 are determined. For example it may be determined which hardware devices, such as a user interface or processor, and software applications are provided in the end user device. In step 304, in response to the software and hardware environment determined, a validation process for testing the software and hardware environment to be compatible with the execution requirements for executing the medical application is set up. The validation process may consist of several validation routines and may further be defined by the order of the validation routines in the validation process. The validation process may be selected from a plurality of predefined validation processes. Setting up the validation process may also, alternatively or in addition, include selecting one or more validation process modules, which may consist of one or more validation routines, from a plurality of predefined validation process modules and assembling a validation process, which may also be referred to as creating a validation map, from the routines.

The end user device 101 is then baselined in step 305. Baselining comprises summarizing properties of the end user device 101, such as lists of configurations, binaries and their checksums. The results of baselining are stored in a Validation Baseline. In an alternative embodiment, step 305 may be omitted. In this case, no Validation Baseline is created.

In step 306, the software and hardware environment are tested according to the validation process. For example, it may be determined, whether certain minimal requirement, such as a speed of a data connection or a processing power, are fulfilled. Based on the results of the testing, a device validation protocol or report is created. Following, in step 307, it is determined based on the results of testing whether the software and hardware environment of the end user device 101 are compatible with the execution requirements.

If it is determined that the software and hardware environment of the end user device 101 are not compatible with the execution requirements, execution of the validation application is terminated in step 308 and receiving and executing the medical application is blocked. Additionally, a black listing, containing values for parameters and/or combinations of values for parameters indicating that the end user device 101 is not compatible for the medical application, may be updated and stored on a server repository based on the results of the testing.

If, in step 307, it is determined that the software and hardware environment of the end user device 101 are compatible with the execution requirements, then, in step 309, the system is baselined again and the result is compared to the Validation Baseline created in step 305 to determine whether the baseline has changed. If the baseline has changed, the validation process returns to step 301 and validation starts over. As explained above with regard to step 301, the user may be prompted to confirm starting the validation process (again). If the user does not confirm starting the validation process, the validation application may be terminated. If it is determined that the baseline has not changed in step 309, step 310 is performed. In embodiments in which step 305 is omitted and no Validation Baseline is created, step 309 is omitted. In this case, if it is determined that the software and hardware environment of the end user device 101 are compatible with the execution requirements in step 307, step 310 is performed.

Step 310 comprises creating a Device State Signature. The Device State Signature may be a secured, for example encrypted, key that represents the checksum of the device validation report and, if applicable, the Validation Baseline. Hereby, the Device State Signature represents the state of the end user device 101 at the time of determining that the software and hardware environment are compatible with the execution requirements. The Device State Signature is stored on the end user device 101 and/or a server repository. Additionally, a white listing containing values for parameters and/or combinations of values for parameters indicating that the end user device 101 is compatible for the medical application, may be updated and stored on a server repository based on the results of the testing. The medical application is then downloaded and installed in the end user device 101. Additionally, the validation application may be amended in step 310. For example, software routines for monitoring the end user device 101 and/or the medical application and/or for triggering re-execution of the validation process may be downloaded and installed.

In step 311, the medical application is then executed in a test mode which shall be broadly construed herein as covering a test mode, a demonstration mode, a validation mode or a preliminary mode. The software and hardware environment are tested to be compatible with execution requirements while the medical application is executed in test mode. The execution requirements may be any or all requirements with regard to which testing was performed in step 306. For example, if in step 306, a processing power was determined to meet minimum requirements for the medical application, it may be tested in step 311, whether processing power is sufficient while running the medical application. Alternatively or additionally, testing may be performed in step 311 with regard to one or more execution requirements with regard to which testing was not performed in step 306. For example, a speed for performing certain software routines specific to the medical application may be determined and compared to a minimum speed requirement. Based on the results of the testing, an application validation protocol or report is created. Following, in step 312, it is determined based on the results of testing, whether the software and hardware environment of the end user device 101 are compatible with the execution requirements while the medical application is executed in demonstration or validation mode.

If it is determined that the software and hardware environment of the end user device 101 are not compatible with the execution requirements, the medical application is marked as unusable and/or is uninstalled from the end user device 101 in step 313. Following, the method proceeds to step 308 in which execution of the validation application is terminated and receiving and executing the medical application is blocked. Additionally, a black listing, containing values for parameters and/or combinations of values for parameters indicating that the end user device 101 is not compatible for the medical application, may be updated and stored on a server repository based on the results of the testing.

If, in step 312, it is determined that the software and hardware environment of the end user device 101 are compatible with the execution requirements, then, in step 314, the system is once again baselined and the result is compared to the Validation Baseline created in step 305 to determine whether the baseline has changed. If the baseline has changed, the validation process returns to step 301 and validation starts over. As explained above with regard to step 301, the user may be prompted to confirm starting the validation process (again). If the user does not confirm starting the validation process, the validation application may be terminated. If it is determined that the baseline has not changed in step 314, step 315 is performed. In embodiments in which step 305 is omitted and no Validation Baseline is created, step 314 is omitted. In this case, if it is determined that the software and hardware environment of the end user device 101 are compatible with the execution requirements in step 312, step 315 is performed.

In step 315, an Application State Signature is created. The Application State Signature may be a secured, for example encrypted, key that represents the checksum of the application validation report and the Device State Signature. The Device State Signature may be included in the Application State Signature entirely, in part, or in a summary such as a checksum. Alternatively, the Device State Signature may not be included in the Application State Signature. Thereby, the Application State Signature represents the state of the end user device 101 at the time of determining that the software and hardware environment are compatible with the execution requirements while the medical application is executed in demonstration or validation mode. The Application State Signature is stored on the end user device 101 and/or a server repository. In an alternative embodiment, the Device State Signature is not stored on a server repository in step 310 and the Device State Signature and the Application State Signature are stored on a server repository, separately or in consolidated form, in step 315. Additionally, a white listing containing values for parameters and/or combinations of values for parameters indicating that the end user device 101 is compatible for the medical application, may be updated and stored on a server repository based on the results of the testing.

Execution of the medical application is then allowed in step 316 and the validation process ends.

Figure 4:
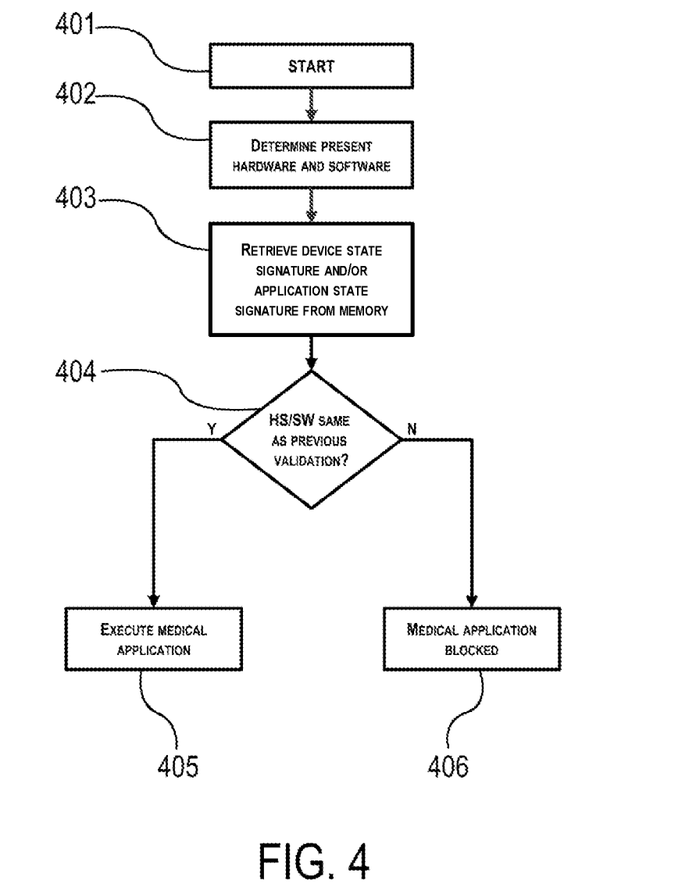
FIG. 4 a flow diagram for steps of a further method for validating a medical application.

The flow diagram in FIG. 4 illustrates steps of a further method for validating a medical application. In the embodiment shown, a present hardware and software environment provided to the end user device 101 are determined every time the medical application is executed.

The medical application is started in step 401. Following, in step 402, the present hardware and software environment provided to the user device 101 are determined. To determine the present hardware and software environment, the end user device 101 is baselined. In step 403, a Device State Signature and/or an Application State Signature are retrieved from the memory 104 of the end user device 101 and/or from a server repository. To compare the present hardware and software environment to the hardware and software environment determined in a validation that was previously performed, the baseline determined in step 402 is compared in step 404 to the Device State Signature and/or the Application State Signature retrieved in step 403.

If it is determined that the present hardware and software environment is the same as the hardware and software environment determined in a previous validation, the medical application is executed in step 405.

If, in step 404, it is determined that the present hardware and software environment is different from the hardware and software environment determined in a previous validation, the medical application is blocked from execution in step 406. The end user device 101 may then return to a normal mode of operation.

Blocking the medical application from execution may comprise suppressing execution of any code of the medical application. Hereby, the medical application may not be started in the end user device 101. Alternatively, blocking the medical application from execution may comprise suppressing execution of only parts of the code of the medical application. For example, when execution of the medical application is blocked, a graphical user interface of the medical application may load, but all data transmission from and to the medical device 102 and other external devices 107 may be blocked by suppressing all execution of the respective elements of the code of the medical application.

Whenever the medical application is blocked from execution, the user may be notified of the blocking. For example, a message may be displayed on a display of the end user device 101 informing the user that the medical application has been blocked from execution. The notification may also comprise the reasons for blocking the medical application from execution and/or the extent of the blocking, such as which functionalities of the medical application have been blocked when the medical application itself is not blocked from loading altogether.

Alternatively, the user may be prompted to start a present validation comprising a present validation process. The present validation may comprise all steps of the previous validation. The previous validation may, for example, comprise all steps described with regard to the embodiment of the method of FIG. 3. Alternatively, steps may be added to and/or deleted in comparison to the previous validation or the present validation may be separate and different from the previous validation.

In a further alternative, the user may not be prompted to start the present validation in step 406. The present validation may be performed automatically.

Figure 5:
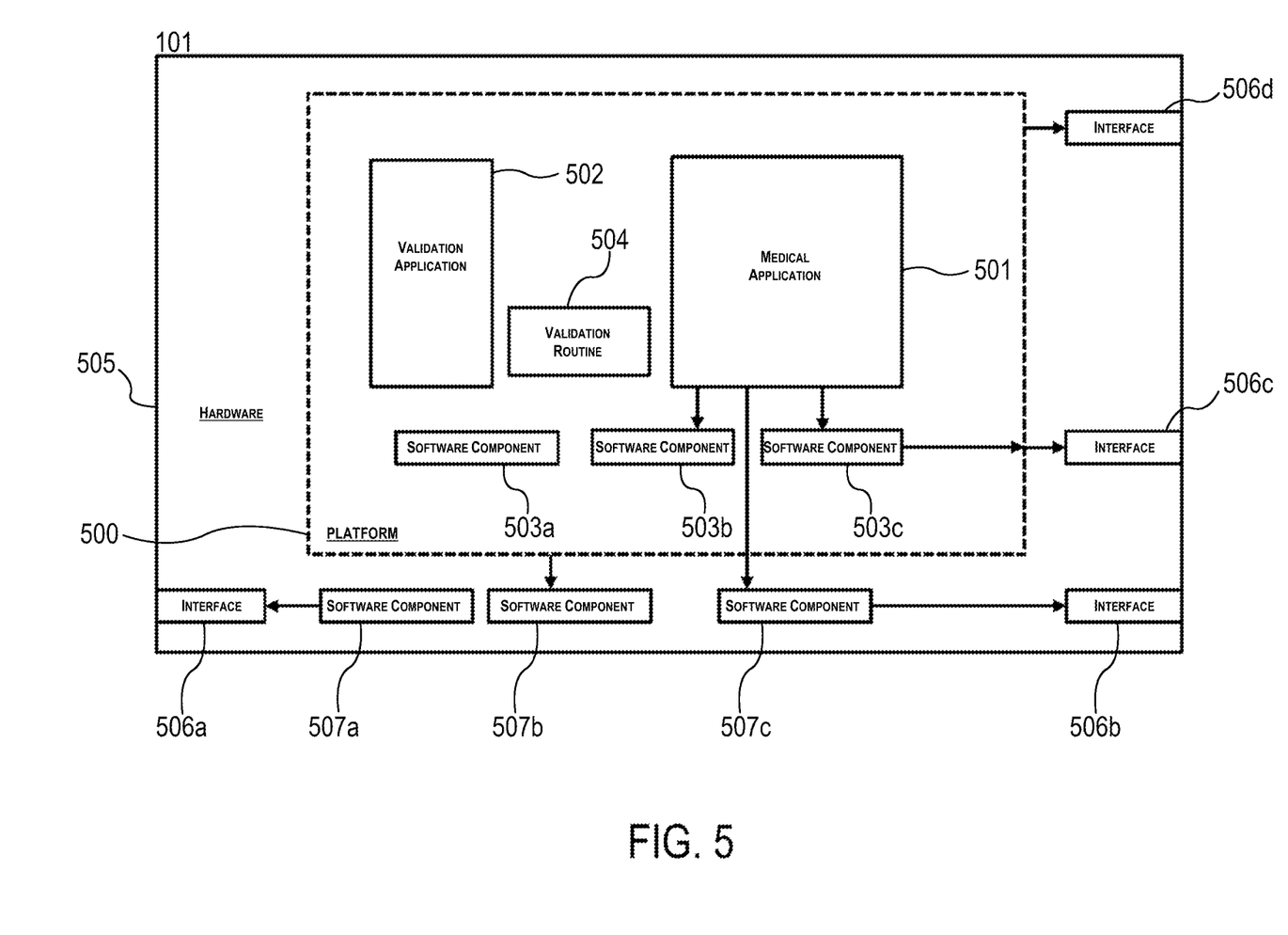
FIG. 5 a schematic illustration of a step of setting up a validation process for the method for validating a medical application.

FIG. 5 is a schematic illustration of a step of setting up a validation process for the method for validating a medical application on the end user device 101. The end user device 101 comprises a platform 500 which may also be referred to as a software domain. The platform 500 may be essentially comprised of an operating system. Several software components run on the platform 500. Software components include the medical application 501, the validation application 502 as well as several software components 503a, . . . , 503c that may form part of the platform 500 itself or may be provided as third-party applications. Additionally, data, such as validation routines 504, may be stored in association with the platform 500 or software components provided thereon. The end user device 101 further comprises a hardware domain 505. The hardware domain comprises hardware components such as different interface devices 506a, . . . , 506d. For example, the interface device 506a may be an optical disk drive and the interface device 506b may be a wireless data communication interface such as a Bluetooth module. Other software components 507a, . . . , 507c may be associated with the hardware domain 500 and not with the platform 500. For example, software components 507a, . . . , 507c may be firmware components.

For setting up a validation process, hardware interface devices and software interface devices provided in the end user device 101 are analyzed. The validation process may be set up based on which components the medical application 501 will interact with. In the embodiment shown in FIG. 5, the medical application 501 interacts with software components 503b, 503c and 507c and with hardware components 506b and 506c. The medical application 501 interacts with hardware component 506b via software component 507c in the hardware domain. Medical application 501 interacts with hardware component 506c via software component 503c and the platform 500.

When the components the medical application interacts with have been determined, the validation process may be set up accordingly. For example, in an embodiment of the method in which the validation process is assembled from predefined validation process modules, for the embodiment of the end user device 101 shown in FIG. 5, validation process modules associated with software components 503b, 503c and 507c and with hardware components 506b and 506c may be chosen to assemble the validation process, but validation process modules associated with software components 503a, 507a, 507b and 507d and with hardware components 506a and 506d may not exist or may exist but may not be included in the validation process.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for validating an end user device for use with a medical application, the method comprising:
   (a) receiving a medical application and a validation application in the end user device;
   (b) executing the validation application, comprising the following steps:
      (i) determining a hardware and software environment of the end user device;
      (ii) providing a validation process compatible with the hardware and software environment of the end user device;
      (iii) executing a test mode of the medical application;
      (iv) running the validation process during the test mode;
      (v) evaluating whether a baseline of the hardware and software environment has changed;
      (vi) determining from running the validation process whether the medical application is compatible with the hardware and software environment of the end user device;
   (c) when the medical application is determined to be compatible with the end user device, generating a validation report and storing the validation report in a non-editable data format in at least one of the end user device and a server; and
   (d) when the medical application is determined to be incompatible with the end user device, at least partially blocking the medical application from execution in the end user device.

2. The method according to claim 1, wherein step (d) includes outputting a notification to the end user device.

3. The method according to claim 1, wherein step (b)(ii) comprises selecting the validation process from a plurality of pre-defined validation processes, each pre-defined process being associated with a particular known hardware or software environment.

4. The method according to claim 1, wherein step (d) comprises blocking at least one functionality of the medical application.

5. The method according to claim 1, further comprising executing a second validation, comprising the following steps:
   determining at least one of a present software environment and a present hardware environment of the user device; and
   when one of the present software environment and the present hardware environment is determined to be different from the software and hardware environment, respectively, determined in step (b)(i), selecting a present validation process for testing the present software and/or the present hardware environment; and
   running the present validation process.

6. The method according to claim 1, further comprising:
   providing a white listing of at least one of software components and hardware components allowed for being provided in the software environment and the hardware environment, respectively, provided to the end user device; and
   determining whether at least one of a hardware component and a software component determined to be provided in the software environment and the hardware environment, respectively, is in the white listing.

7. The method according to claim 1, further comprising:
   providing a black listing of at least one of software components and hardware components not allowed for being provided in the software environment and the hardware environment, respectively, provided to the end user device; and
   determining whether at least one of a hardware component and a software component determined to be provided in the software environment and the hardware environment, respectively, is in the black listing.

8. The method according to claim 1, wherein step (b) comprises executing a user interaction routine configured to test a user interface of the end user device.

9. The method according to claim 1, wherein the executing of the validation application further comprises executing the medical application in demonstration mode.

10. An end user device for data communication with a medical device, comprising:
    a processor;
    a medical application configured to provide data communication between the end user device and a medical device; and
    a validation application configured to:
       (i) determine a hardware and software environment of the end user device;
       (ii) select a validation process compatible with the hardware and software environment of the end user device;
       (iii) execute a test mode of the medical application;
       (iv) run the validation process during the test mode;
       (v) evaluate whether a baseline of the hardware and software environment has changed;
       (vi) determine from running the validation process whether the medical application is compatible with the end user device;
    wherein when the medical application is determined to be compatible with the end user device, a validation report is generated and the validation report is stored in a non-editable data format in at least one of the end user device and a server; and
    when the medical application is determined to be incompatible with the end user device, the medical application is at least partially blocked from execution on the end user device.

11. A medical system, comprising:
    a medical device; and
    an end user device comprising:
       a processor;
       a medical application configured to provide data communication between the end user device and the medical device; and
       a validation application configured to:
          (i) determine a hardware and software environment of the end user device;
          (ii) select a validation process compatible with the hardware and software environment of the end user device;
          (iii) execute a test mode of the medical application;
          (iv) run the validation process during the test mode;
          (v) evaluate whether a baseline of the hardware and software environment has changed;
          (vi) determine from running the validation process whether the medical application is compatible with the end user device;
       wherein when the medical application is determined to be compatible with the end user device, a validation report is generated and the validation report is stored in a non-editable data format in at least one of the end user device and a server; and when the medical application is determined to be incompatible with the end user device, the medical application is at least partially blocked from execution on the end user device.

\* \* \* \* \*